(12) United States Patent
Kim et al.

(10) Patent No.: US 10,506,970 B2
(45) Date of Patent: Dec. 17, 2019

(54) METHOD AND APPARATUS FOR MONITORING CONSCIOUSNESS

(71) Applicants: InBody Co., Ltd., Seoul (KR);
University of Ulsan Foundation For Industry Cooperation, Ulsan (KR);
POSTECH ACADEMY-INDUSTRY FOUNDATION, Pohang-si, Gyeongsangbuk-do (KR)

(72) Inventors: Seunghwan Kim, Pohang-si (KR);
Woo-Sung Jung, Pohang-si (KR);
Heonsoo Lee, Pohang-si (KR);
Gyujeong Noh, Seoul (KR); Ki Chul Cha, Seoul (KR); Jong Keun Kim, Gwangju-si (KR); Jong Ku Lee, Incheon (KR)

(73) Assignees: INBODY CO., LTD., Seoul (KR);
UNIVERSITY OF ULSAN FOUNDATION FOR INDUSTRY COOPERATION, Ulsan (KR);
POSTECH ACADEMY-INDUSTRY FOUNDATION, Pohang-si (KR)

( * ) Notice: Subject to any disclaimer, the term of this patent is extended or adjusted under 35 U.S.C. 154(b) by 432 days.

(21) Appl. No.: 15/391,412

(22) Filed: Dec. 27, 2016

(65) Prior Publication Data
US 2017/0181693 A1  Jun. 29, 2017

(30) Foreign Application Priority Data

Dec. 29, 2015  (KR) .................... 10-2015-0188334

(51) Int. Cl.
*A61B 5/0476* (2006.01)
*A61B 5/04* (2006.01)
*A61B 5/00* (2006.01)

(52) U.S. Cl.
CPC ........ *A61B 5/4821* (2013.01); *A61B 5/04012* (2013.01); *A61B 5/0476* (2013.01)

(58) Field of Classification Search
CPC .............. A61B 5/4821; A61B 5/04012; A61B 5/04014; A61B 5/0476; A61B 5/048
(Continued)

(56) References Cited

U.S. PATENT DOCUMENTS 6,631,291 B2 * 10/2003 Viertio-Oja .......... A61B 5/0476
600/544
6,731,975 B1 * 5/2004 Viertio-Oja .......... A61B 5/0476
600/544
(Continued)

FOREIGN PATENT DOCUMENTS

EP      2789293 A1   10/2014
KR  20090115306 A   11/2009

OTHER PUBLICATIONS

Uncheol Lee et al., Genuine and Spurious Phase Synchronization Strengths during Consciousness and General Anesthesia, 2012, pp. 1-11, vol. 7, Issue 10, PLOS ONE.
(Continued)

*Primary Examiner* — Navin Natnithithadha
(74) *Attorney, Agent, or Firm* — Cantor Colburn LLP

(57) ABSTRACT

Disclosed is a method of monitoring consciousness, the method including sensing at least two brainwave signals, extracting respective phase signals from the sensed brainwave signals, calculating entropy based on a variety in a change in terms of a phase difference between the extracted phase signals, and assessing a state of consciousness based on the calculated entropy.

9 Claims, 20 Drawing Sheets

(58) Field of Classification Search
USPC .................................................. 600/544–545
See application file for complete search history.

(56) References Cited

U.S. PATENT DOCUMENTS

| | | | | |
|---|---|---|---|---|
| 6,801,803 | B2 * | 10/2004 | Viertio-Oja | A61B 5/0476 600/300 |
| 7,228,169 | B2 | 6/2007 | Viertio-Oja et al. | |
| 7,299,088 | B1 * | 11/2007 | Thakor | A61B 5/048 600/544 |
| 7,697,979 | B2 * | 4/2010 | Martinerie | A61B 5/0006 600/544 |
| 7,725,174 | B2 * | 5/2010 | Kern | A61B 5/4821 600/544 |
| 2008/0021345 | A1 * | 1/2008 | Kern | A61B 5/0476 600/554 |
| 2013/0245485 | A1 | 9/2013 | Mashour et al. | |

OTHER PUBLICATIONS

Uncheol Lee et al., The directionality and functional organization of frontoparietal connectivity during consciousnes and anesthesia in humans, 2009, pp. 1069-1078, Elsevier Inc.

Aylin Cimenser et al., "Tracking brain states under general anesthesia by using global coherence analysis," Proceedings of the National Academy of Sciences (PNAS), 2011, pp. 8832-8837, vol. 108, No. 21.

Bernard J. Baars, "A cognitive theory of consciousness" 1988, 300 pages, U.S.A.

E. Olofsen et al., "Permutation entropy of the electroencephalogram: a measure of anaesthetic drug effect," British Journal of Anaesthesia, 2008, pp. 810-821, vol. 101.

Gernot G. Supp et al., "Cortical hypersynchrony predicts breakdown of sensory processing during loss of consciousness," Current Biology 21, 2011, pp. 1988-1993, Elsevier Ltd.

Heonsoo Lee et al., "Reconfiguration of Network Hub Structure after Propofol-induced Unconsciousness," Anesthesiology, 2013, pp. 1347-1359, vol. 119, No. 6.

Jorgen Bruhn et al., "Approximate entropy as an electroencephalographic measure of anesthetic drug effect during desflurane anesthesia," Anesthesiology, 2000, pp. 715-726, vol. 92, No. 3.

Patrick L. Purdon et al., "Electroencephalogram signatures of loss and recovery of consciousness from propofol," PNAS, 2013, pp. E1142-E1151.

Stanislas Dehaene et al., "Toward a computational theory of conscious processing," Current Opinion in Neurobiology, Apr. 2014, 16 pages.

Uncheol Lee et al., "Genuine and Spurious Phase Synchronization Strengths during Consciousness and General Anesthesia," PLOS ONE, Oct. 2012, 11 pages (e46313), vol. 7.

* cited by examiner

METHOD AND APPARATUS FOR MONITORING CONSCIOUSNESS

CROSS-REFERENCE TO RELATED APPLICATION(S)

This application claims the priority benefit of Korean Patent Application No. 10-2015-0188334 filed on Dec. 29, 2015, in the Korean Intellectual Property Office, the disclosure of which is incorporated herein by reference for all purposes.

BACKGROUND

1. Field

One or more example embodiments relate to a method and apparatus for monitoring a state of consciousness, and more particularly, to a method and apparatus for monitoring a state of consciousness of a human being or a patient in response to administration of a drug.

2. Description of Related Art

A surgery patient or a critically ill patient may need an appropriate level of hypnosis to prevent stress from a surgical operation, or awareness or memory of the surgical operation, and thus rapid and accurate determination of a depth of anesthesia may be important and essential in managing or controlling anesthesia during and after the surgical operation.

In a process of conducting a medical treatment for a patient, a method of anesthetizing the patient may be classified into inhalation anesthesia and intravenous anesthesia. For the intravenous anesthesia, a sedative and an analgesic may be used simultaneously. However, administering an excessive dose of such anesthetic drugs to a patient may leave the patient being in a serious condition, for example, a respiratory failure and a drop in heart rate and blood pressure, and thus monitoring a state or a condition of the patient and administering an appropriate dose of an anesthetic drug may be needed.

To determine a minimum dose of an anesthetic drug having a sufficient anesthetic effect on a patient, quantitative measurement of an anesthetic effect may be needed. For the inhalation anesthesia, a single drug having both a sedative effect and an analgesic effect may be used to anesthetize a patient. However, the effects may not be individually adjustable. In contrast, in a case of the intravenous anesthesia, a sedative and an analgesic may be individually administered, and thus adjusting a concentration of each of the sedative and the analgesic may be possible as necessary. The two anesthesia methods described in the foregoing may be used selectively or by mixture depending on a state of a patient. Thus, for effective anesthesia, how each of a sedative and an analgesic affects a patient may need to be measured quantitatively.

A bispectral index (BIS) is generally used as an index indicating a sedative effect of an anesthetic drug that is currently used during a surgery to measure a state of consciousness of a patient using a frequency and a phase of a brainwave.

The BIS may be a simplified numerical value indicating a level of sedation and hypnosis induced by an anesthetic or a sedative, and determined by measuring a frequency, amplitude, and coherence in an electroencephalogram (EEG). The BIS may be indicated as a score from 0 to 100, which indicates a state from an alert state to an unconscious state, through an algorithm-based analysis and processing performed on a degree of a change in an electrical activity of a cerebral cortex that may be induced by anesthesia. In detail, the BIS may be a method of analyzing a signal detected from an electrode and indicating a level of sedation of an anaesthetized patient as a score out of 100. Here, 100, a highest score, may indicate a fully conscious state and 0, a lowest score, may indicate an unconscious state with a flat-lined EEG indicating that a brainwave is not completely detected.

Recently, a probability of an error in a BIS monitor has continued to be reported. It is reported that approximately 14 seconds to 155 seconds are delayed for updating a BIS due to a complex anesthetic depth algorithm of the BIS monitor. Such a delay in calculating a BIS may demonstrate a limitation of the BIS monitor as a patient monitoring device to prevent the patient from being alert or awake and forming memories during a surgical operation.

An anesthetic depth monitoring device of a General Electric (GE) company may assess a depth of anesthesia by using an index, for example, a spectral entropy (GE Healthcare, Helsinki, Finland) based on a brainwave and an electromyogram (EMG), and presenting two types of values, for example, a state entropy (SE) and a response entropy (RE). However, there may be a high probability of an error in such a device due to an influence of using a muscle relaxant.

In addition, the BIS monitor and the GE device may not consider a functional connectivity between different cerebral cortices. For example, according to recent papers entitled "Cortical hypersynchrony predicts breakdown of sensory processing during loss of consciousness" published in Current Biology 21, 1988-1993 (2011), by Supp G G, Siegel, M., Hipp J. F., and Engel A. K, entitled "Tracking brain states under general anesthesia by using global coherence analysis" published in Proceedings of the National Academy of Sciences (PNAS) 108, 8832-8837 (2011), by Cimenser A. et al., and entitled "Electroencephalogram signatures of loss and recovery of consciousness from propofol" published in PNAS 110, E1142-E1151 (2013), by Purdon P. L. et al., an increase in connectivity in a prefrontal or frontal region may have a close correlation with loss of consciousness and a decrease in a level of consciousness. However, descriptions in the papers may not be applicable to an anesthetic depth monitoring device because the papers describe a need of 128 sensors with a high-resolution EEG to quantify the functional connectivity.

For another example, a related art, US 2013/0245485 A1, discloses technology for measuring a depth of anesthesia based on an intensity or strength of a connectivity between brainwave signals by determining a directional feedback connectivity and monitoring a feedback activity of a patient. However, according various research papers, for example, some papers published in Anesthesiology 119, 1347 (2013), by H. Lee, G A. Mashour, G J. Noh, S. Kim, and U. Lee, and published in Public Library of Science (PLoS) One 7, e46313 (2012), by U. Lee, H. Lee, M. Müller, G J. Noh, and G A Mashour, a strength of a connectivity between signals of cortices may increase or decrease after anesthesia. As described above, there are various research results associated with a correlation between a strength of a connectivity between brainwave signals and a depth of anesthesia. Thus, a consistent conclusion about an anesthetic state may not be drawn from a strength of a connectivity between brainwave signals, and thus there is still a limitation in using information associated with a strength of a connectivity between brainwave signals as an index of a depth of anesthesia.

In addition, the related art, US 2013/0245485 A1, discloses only a technology for assessing and determining a functional connectivity between brainwave signals using a phase lag index (PLI) and a directed phase lag index (dPLI) obtained by applying a Heaviside step function to the PLI. However, such technology may have a limitation in accurately assessing a complexity of a connectivity between brainwave signals, which will be described later in the present disclosure.

For still another example, another related art, KR 2009-0115306 A1 and U.S. Pat. No. 7,228,169 B1, discloses a method of determining a level of consciousness of a patient by comparing a measured signal and a reference signal. However, using only a single signal may not be sufficient to determine a complexity of a connectivity between brain regions.

As described above, assessing a depth of anesthesia may be highly significant for a surgery requiring general anesthesia, and thus numerous studies are being conducted in order to objectively assess a depth of anesthesia. However, a complete anesthetic depth monitoring device is yet to be developed, and a device may only monitor each level of consciousness.

SUMMARY

An aspect provides a method and apparatus for monitoring a state of consciousness that may measure a depth of anesthesia by detecting a complexity in a connection among brainwave signals through an analysis based on time and space information of the brainwave signals sensed in a plurality of portions of a human body, in order to solve issues such as, for example, a time delay in measuring a depth of anesthesia due to a complicated algorithm, an issue of not considering an influence of a connection between different cerebral cortical regions on consciousness due to a single signal-based algorithm, and an issue of not quantifying a dynamic characteristic of a connection by considering only a statistical characteristic of a phase difference or the connection.

Another aspect provides a method and apparatus for monitoring a state of consciousness that may minimize a time delay in measuring a depth of anesthesia by simplifying an information processing process in detecting a complexity of a connection among brainwave signals.

According to an aspect, there is provided a method of monitoring a state of consciousness, the method including sensing at least two brainwave signals, extracting respective phase signals from the sensed brainwave signals, patterning a phase difference between the extracted phase signals, calculating entropy based on a variety of patterns, and assessing a state of consciousness based on the calculated entropy.

The brainwave signals may be sensed from different cerebral regions.

The patterning of the phase difference may include converting a magnitude of the phase difference to a base-N number based on a result of comparing the magnitude of the phase difference and N reference values, in which N denotes a natural number greater than or equal to 2.

N may denote 2.

The patterning of the phase difference may include dividing the phase difference converted to the base-N number into patterns based on a preset bit number.

According to another aspect, there is provided an apparatus for monitoring a state of consciousness, the apparatus including a sensor configured to sense at least two brainwave signals, a calculator configured to pattern a phase difference between respective phase signals of the sensed brainwave signals and calculate entropy based on a variety of patterns, and a display configured to display the calculated entropy.

In an example, the calculator may include a phase information extractor configured to extract a first phase signal and a second phase signal, respectively, from the brainwave signals.

In another example, the calculator may include a phase information extractor configured to extract a first phase signal and a second phase signal, respectively, from the brainwave signals, and a base-N number converter configured to convert, to a base-N number, a magnitude of a phase difference between a sampled first phase signal and a sampled second phase signal obtained by sampling the extracted first phase signal and the extracted second phase signal based on a preset sampling period, based on a result of comparing the magnitude of the phase difference and N reference values, in which N denotes a natural number greater than or equal to 2.

In still another example, the calculator may include a phase information extractor configured to extract a first phase signal and a second phase signal, respectively, from the brainwave signals, a base-N number converter configured to convert, to a base-N number, a magnitude of a phase difference between a sampled first phase signal and a sampled second phase signal obtained by sampling the extracted first phase signal and the extracted second phase signal based on a preset sampling period, based on a result of comparing the magnitude of the phase difference and N reference values, in which N denotes a natural number greater than or equal to 2, and a patterner configured to perform patterning on a digital signal converted from the base-N number to generate a pattern having a preset bit number.

In yet another example, the calculator may include a phase information extractor configured to extract a first phase signal and a second phase signal, respectively, from the brainwave signals, a base-N number converter configured to convert, to a base-N number, a magnitude of a phase difference between a sampled first phase signal and a sampled second phase signal obtained by sampling the extracted first phase signal and the extracted second phase signal based on a preset sampling period, based on a result of comparing the magnitude of the phase difference and N reference values, in which N denotes a natural number greater than or equal to 2, a patterner configured to perform patterning on a digital signal converted from the base-N number to generate a pattern having a preset bit number, and an entropy analyzer configured to calculate entropy based on a variety of generated patterns.

According to still another aspect, there is provided a non-transitory computer-readable storage medium storing a program to cause computing hardware to sense at least two brainwave signals, extract respective phase signals from the sensed brainwave signals, pattern a phase difference between the extracted phase signals, calculate entropy based on a variety of patterns, and assess a state of consciousness based on the calculated entropy.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which.

DETAILED DESCRIPTION

Figure 1:
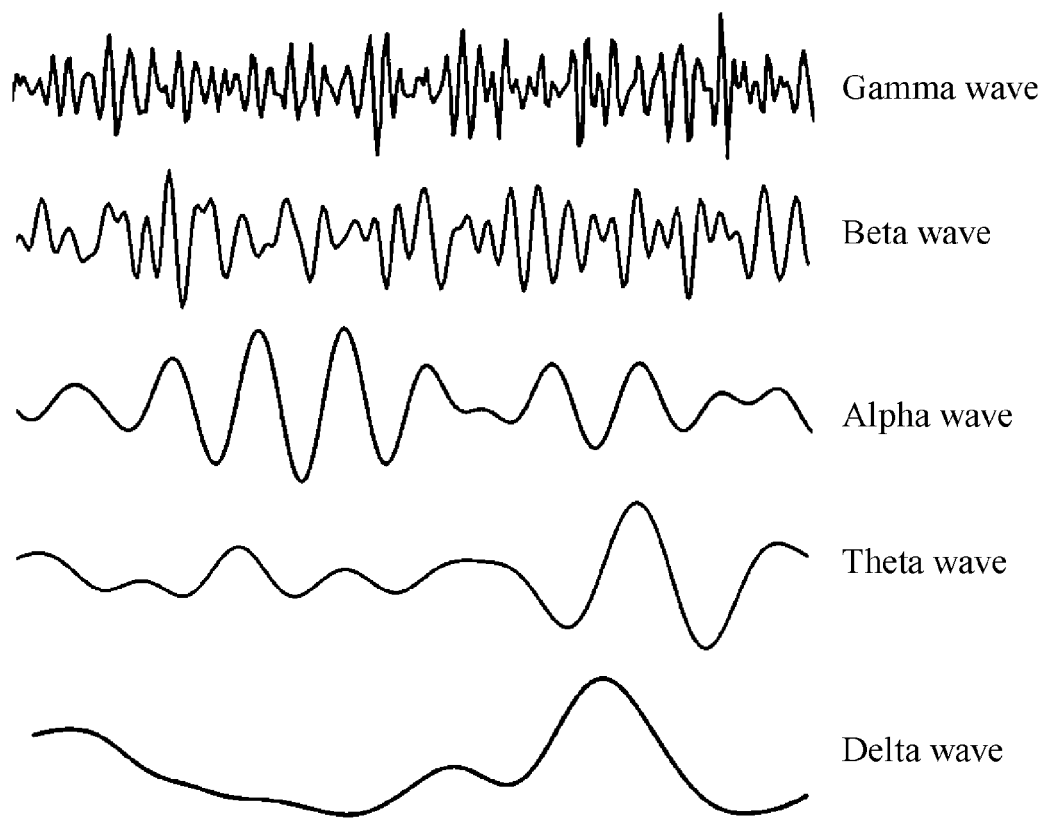
FIG. 1 is a diagram illustrating types of a brainwave.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure. It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Application of Example Embodiments of the Present Disclosure

Example embodiments described herein may be used to monitor a depth of consciousness, a depth of unconsciousness, a depth of anesthesia, a state of alertness or vigilance of a subject, for example, a patient, a depth of sedation, a state of hypnosis, a state of concentration, and a state of attention.

<Types of Brainwave>

FIG. 1 is a diagram illustrating types of a brainwave.

Example embodiments described herein may be used to monitor at least one of a degree of anesthesia or a state of consciousness of a patient while an anesthetic drug is being administered to the patient to enable the patient to be sedated during a medical procedure being performed on the patient.

According to example embodiments, a target to be measured may be a biosignal of an individual, and the biosignal may be a brainwave, for example, an electroencephalogram (EEG). The EEG refers to an electrical flow that may be generated when a signal is transferred between brain nerves in a nervous system. In detail, the EEG may be formed by an activity of an inhibitory postsynaptic potential (IPSP) and an excitatory postsynaptic potential (EPSP) of a cone cell. Referring to FIG. 1, a brainwave may be classified into a gamma wave, a beta wave, an alpha wave, a theta wave, and a delta wave based on a state of a human being.

The gamma wave may be a pattern of oscillation, which is more rapid than the beta wave, with a frequency between 41 hertz (Hz) and 50 Hz, and it is reported that the gamma wave is closely associated with an emotionally exited state, or with a highly cognitive information processing such as, for example, inference and decision.

The beta wave may be a pattern of oscillation that is shown mainly in a frontal region with a frequency between 13 Hz and 40 Hz, and may be observed during a psychological activity, for example, being awake and speaking. In addition, the beta wave may be predominantly observed in an anxious or nervous state, and when a complex calculation is processed.

The alpha wave may be a pattern of oscillation that is observed mainly in an easy or comfortable state such as, for example, when tension is relaxed, with a frequency between 8 Hz and 12 Hz, and may have amplitude that increases in a more stable and comfortable state. In general, a regular wave may be observed in succession, and a magnitude or amplitude of the alpha wave may be greatest in a parietal region and an occipital region and smallest in a frontal region. A stable or steady alpha wave may be observed when a person is in a relaxed state with eyes closed, and the alpha wave may be inhibited when the person opens the eyes and looks at an object or is psychologically excited. Such a phenomenon is referred to as alpha inhibition. The alpha wave is closely associated with development of a brain, and is measured at a frequency of approximately 6 Hz in infancy, and the frequency increases when a human being ages.

The theta wave may be a pattern of oscillation that is mainly observed in a transient state leading to an emotionally stable state or a sleep state, with a frequency between 4 Hz and 7 Hz, and may be more frequently observed in a child than an adult. It is reported that the theta wave is associated with various states, for example, memory, creativity, concentration, and relieving anxiety (ataraxia). However, standardized results are yet to be released due to different experiment protocols and different characteristics of subjects for experiments, and inconsistent directions of an increase and/or decrease for each cerebral cortical region.

The delta wave may be a pattern of oscillation that is conspicuously observed mainly in a deep sleep state of a normal person or in an infant, with a frequency between 0 Hz and 4 Hz. When a delta wave exceeding an average range appears in a person being awake, the delta wave may be associated with a malignant tumor in a cerebral cortical region, or a disease related to anesthesia or coma. When a delta wave is conspicuously observed in a normal healthy person, noise may be mixed when measuring a brainwave of the person. A frequency domain of the noise may nearly correspond to a frequency domain of the delta wave, and thus the delta wave may appear to be increased. Thus, due to a high probability of noise being mixed in long-time measurement of a brainwave, whether power of a delta wave increases or decreases may not be considered.

A brain may involve interactions among more than ten billion neurons through more than ten trillion neural connections. The neurons may communicate with one another through an elaborately-organized system including an electrical and chemical transfer system of information. According to example embodiments described herein, dissimilar to related technology for modeling a complex and difficult biochemical and mathematical structure based on numerous complex structures and functions of the brain, there is provided a simple mathematical model-based algorithm associated with the interaction in the brain to verify a complexity of connections of information of the brain based on a continuity of the connections of information flows of the brain and a relationship among the connections, and thus a depth of anesthesia may be measured more rapidly and accurately.

In a conscious state, an interaction among signals from brain regions, for example, a connectivity, may be complex. In contrast, in an anesthetic state, such an interaction or a connectivity may be more simplified. For example, according to a book entitled "A cognitive theory of consciousness" published in 1993 by an author, Bernard J. Baars, and a research paper entitled "Toward a computational theory of conscious processing" published in Current Opinion in Neurobiology 25C, 76, in 2014, by S Dehaene, L Charles, J R King, and S Marti, it is derived that flexible neural communication may be required in a conscious state, and a simple connectivity may indicate that the flexible neural communication is disturbed. In addition, according to research papers entitled "Approximate entropy as an electroencephalographic measure of anesthetic drug effect during desflurane anesthesia" published in Anesthesiology 92, p 715, in 2000, by J Bruhn, H Ropcke, and A Hoeft, and entitled "Permutation entropy of the electroencephalogram: a measure of anaesthetic drug effect" published in British Journal of Anaesthesia, Volume 101, p 810, in 2008, by E Olofsen, J W Sleigh, and A Dahan, it is derived that a complexity of a connection between EEG signals may be reduced in consideration of a reduced complexity of an EEG signal itself.

<An Apparatus for Monitoring a State of Consciousness>

Figure 2:
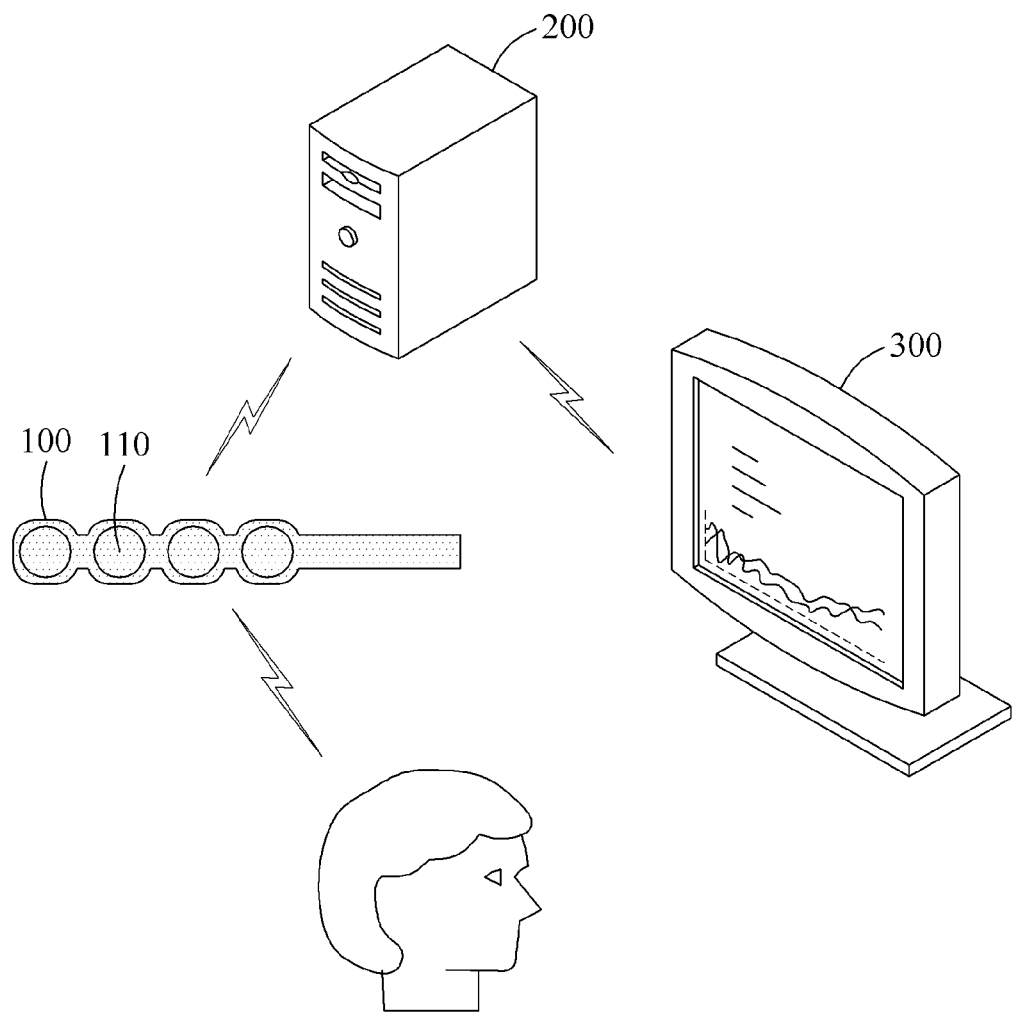
FIG. 2 is a diagram illustrating an apparatus for monitoring a state of consciousness according to an example embodiment.

FIG. 2 is a diagram illustrating an apparatus for monitoring a state of consciousness according to an example embodiment. Hereinafter, the apparatus for monitoring a state of consciousness will be simply referred to as a consciousness state monitoring apparatus 10.

Referring to FIG. 2, the consciousness state monitoring apparatus 10 includes a sensor 100, a calculator 200, and a display 300.

The sensor 100 may sense or measure a biosignal of an individual, and include a plurality of electrode portions 110.

The electrode portions 110 may be a dry electrode, or a wet electrode.

The electrode portions 110 may be attached to a portion of a human body, for example, a head, a scalp, skin, a surface of a brain, a forehead, a skull, a periauricular region, an ear, a face, and a temple. However, the portion to which the electrode portions 110 are to be attached is not limited to the examples described in the foregoing, and the electrode portions 110 may be attached to any portions of a human body from which a brainwave signal is measurable. In addition, the electrode portions 110 may be attached to different regions of the human body.

The electrode portions 110 may be attached to the human body through any one of an adhesion method, a fixing method, an insertion method, and a contactless method.

Each of the electrode portions 110 may include an electrode, and a substrate configured to support the electrode and including a signal wiring providing an electrical signal from the electrode to the calculator 200. The substrate may be flexible, but not limited thereto. A plurality of electrodes may be arranged in a single substrate, and the electrodes may be arranged in a plurality of substrates, respectively.

The sensor 100 may include a filter configured to eliminate noise in an analog signal detected from each of the electrodes in the electrode portions 110, and also include a differential amplifier configured to amplify a signal.

In a case of the electrode portions 110 being a wet electrode, a couplant (or a coupling medium), for example, water, alcohol, oil, hydrogel, and glycerin, may be included.

The calculator 200 may extract a phase signal from each of at least two brainwave signals, or EEG signals, sensed by the electrode portions 110, symbolize a phase relationship between the brainwave signals based on the extracted phase signals, and calculate a phase lag entropy (PLE) to assess a complexity of a connection between the brainwave signals based on the binarized phase relationship. Thus, the calculator 200 may output entropy indicating an influence of a connection between different cerebral cortical regions on consciousness and indicating a dynamic characteristic of the connection.

The display 300 may receive a result of the calculating from the calculator 200, and display the received result. Here, the display 300 may convert the result of calculating the PLE to a form that an observer may easily recognize, for example, a simple numerical value, and display the converted result. The display 300 may also display a curve indicating a signal detected from the sensor 100, and that is, amplitude of an electrical activity based on a lapse of time.

The display 300 may include at least one of, for example, a liquid crystal display (LCD), a thin-film-transistor liquid-crystal display (TFT LCD), an organic light-emitting diode (OLED), a flexible display, and a 3D display.

<Calculator According to an Example Embodiment>

Figure 3:
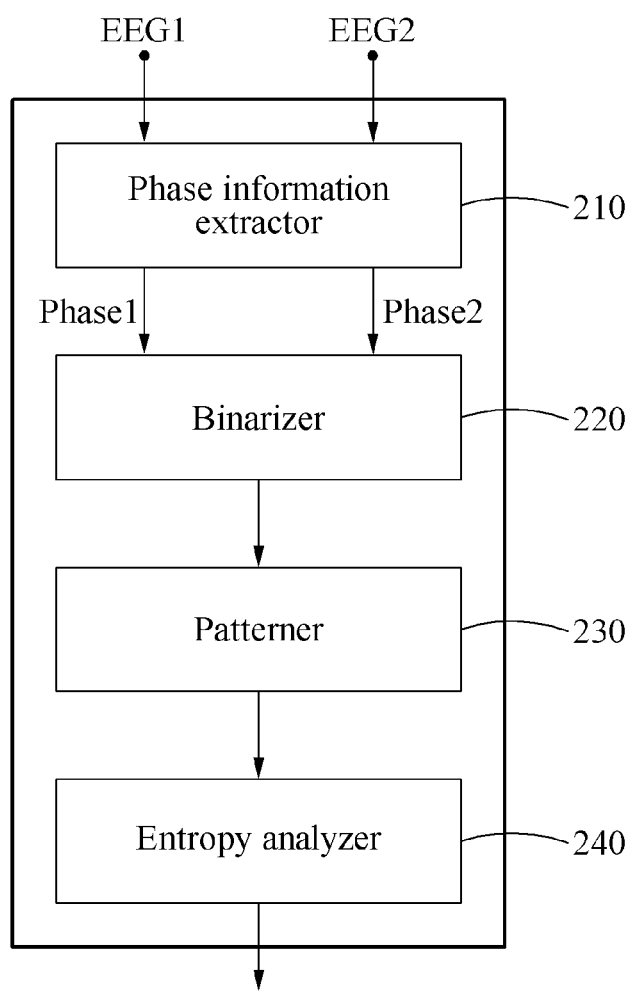
FIG. 3 is a diagram illustrating a calculator according to an example embodiment.
Figure 4:
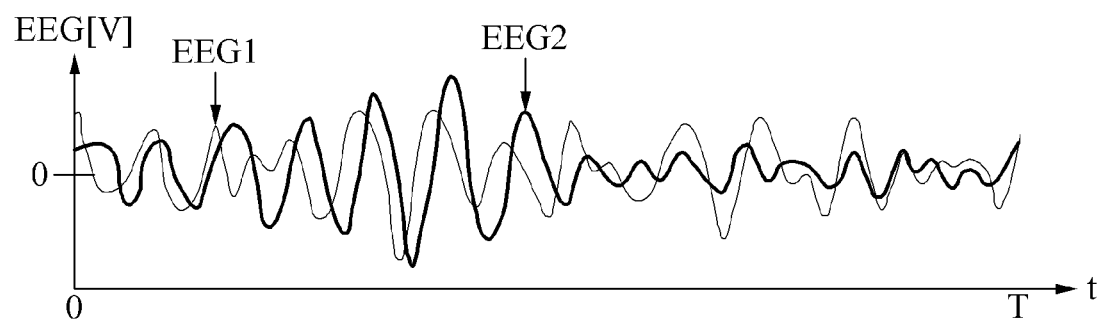
FIG. 4 is a diagram illustrating a waveform of a first electroencephalogram (EEG) signal and a second EEG signal based on time.
Figure 5:
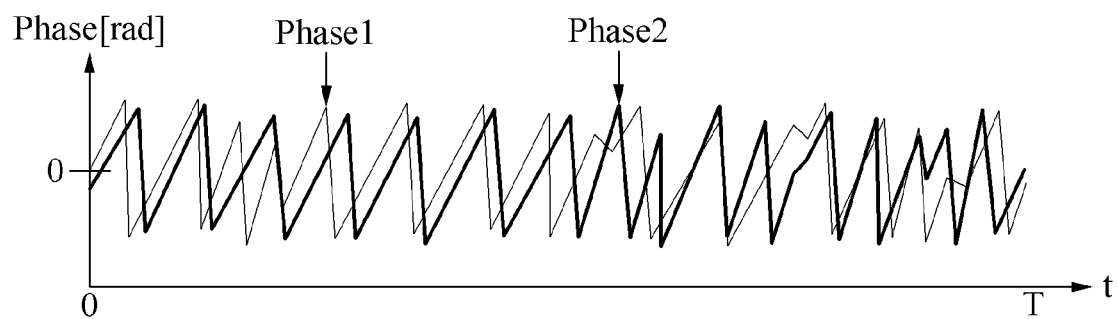
FIG. 5 is a diagram illustrating a waveform of a first phase signal and a second extracted, respectively, from the first EEG signal and the second EEG signal of FIG. 4 based on time.
Figure 6:
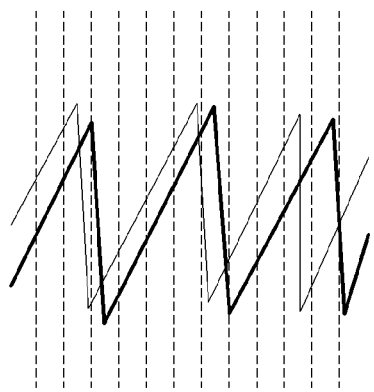
FIG. 6 is a diagram illustrating a waveform obtained by sampling the first phase signal and the second phase signal of FIG. 5 based on a preset sampling period.
Figure 7:
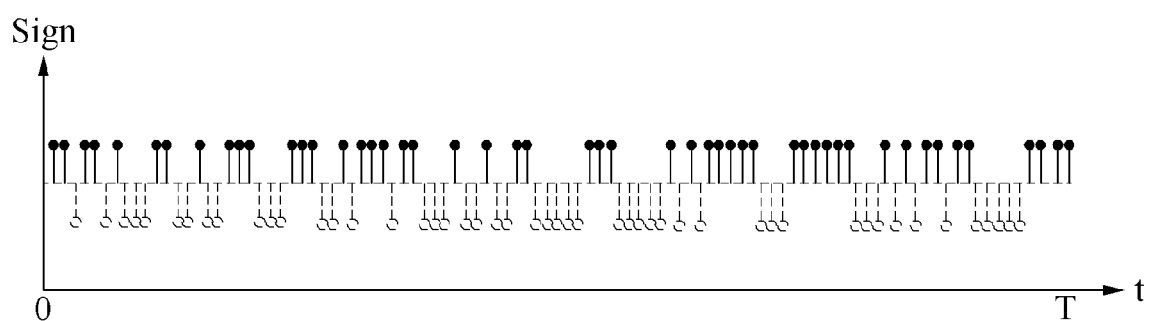
FIG. 7 is a binary graph illustrating a relationship between the sampled first phase signal and the sampled second phase signal of FIG. 6 in terms of leading and lagging behind based on time.
Figure 8:
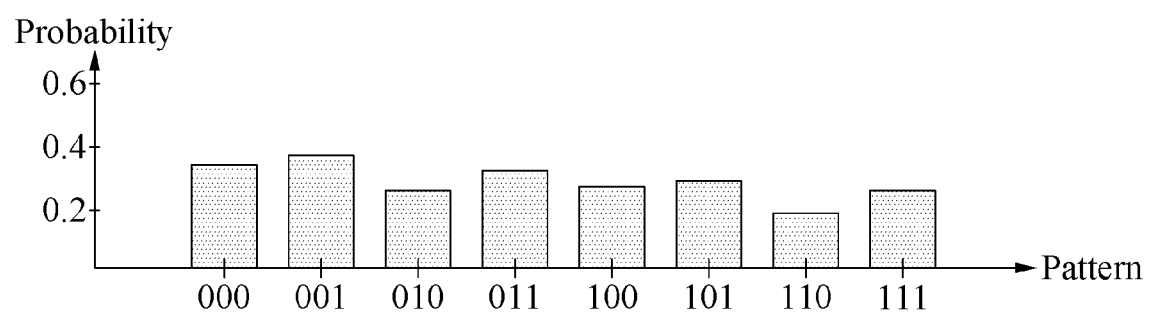
FIGS. 8 and 9 are diagrams illustrating a probability of each pattern being generated.
Figure 9:
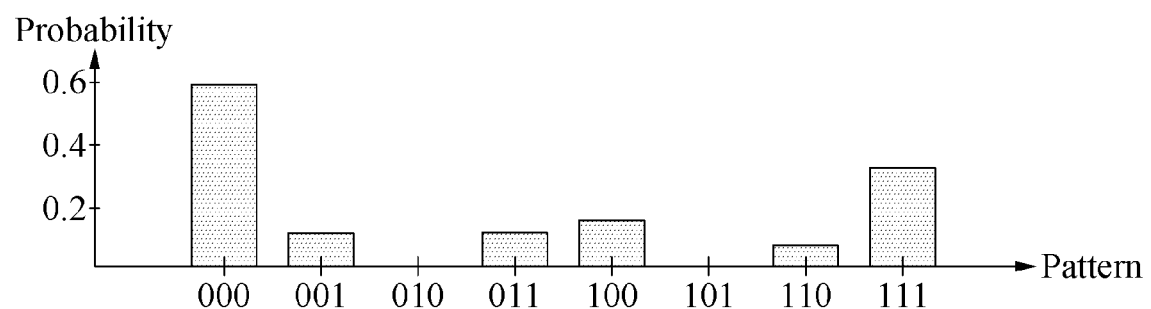

FIG. 3 is a diagram illustrating a calculator according to an example embodiment. FIG. 4 is a diagram illustrating a waveform of a first EEG signal and a second EEG signal based on time. FIG. 5 is a diagram illustrating a waveform of a first phase signal and a second extracted, respectively, from the first EEG signal and the second EEG signal of FIG. 4 based on time. FIG. 6 is a diagram illustrating a waveform obtained by sampling the first phase signal and the second phase signal of FIG. 5 based on a preset sampling period. FIG. 7 is a binary graph illustrating a relationship between the sampled first phase signal and the sampled second phase signal of FIG. 6 in terms of leading and lagging behind based on time. FIGS. 8 and 9 are diagrams illustrating a probability of each pattern being generated.

Referring to FIG. 3, the calculator 200 includes a phase information extractor 210, a binarizer 220, a patterner 230, and an entropy analyzer 240.

The phase information extractor 210 may extract phase information of each of a first brainwave signal EEG1 and a second brainwave signal EEG2 detected by the sensor 100. The phase information extractor 210 may extract a first phase signal Phase 1 from the first brainwave signal EEG1 and a second phase signal Phase2 from the second brainwave signal EEG2.

To extract the first and second phase signals from the first and second brainwave signals, respectively, a well-known method such as Hilbert transform or a wavelet transform may be used. However, the method is not limited to the examples described in the foregoing, and thus any signal transform method that may extract phase information from a signal may be used.

For example, the Hilbert transform may delay, by 90 degrees(°, a frequency component of each of the first brainwave signal EEG1 and the second brainwave signal EEG2 as illustrated in FIG. 4, and extract the first phase signal Phase1 and the second phase signal Phase2 as illustrated in FIG. 5.

Also, the first phase signal Phase1 and the second phase signal Phase2, which are respective phase signals of the first brainwave signal EEG1 and the second brainwave signal EEG2 observed during a preset time interval T, may be extracted from the first brainwave signal EEG1 and the second brainwave signal EEG2 during the time interval T.

The binarizer 220 may configure a phase signal having successive data values to be a finite number of symbols. In detail, successive signals, the input first phase signal Phase1 and the input second phase signal Phase2, may be sampled on a preset sampling period to be discrete signals as illustrated in FIG. 6. In addition, a relationship in terms of leading and lagging of the sampled first phase signal Phase Sam1 and the sampled second phase signal Phase Sam2 may be determined. For example, based on the sampled second phase signal Phase Sam2, whether the sampled first phase signal Phase Sam1 leads or lags behind the sampled second phase signal Phase Sam2 may be determined. Further, such a phase relationship between the sampled first phase signal Phase Sam1 and the sampled second phase signal Phase Sam2 may be binarized. For example, in a case that the sampled first phase signal Phase Sam1 is ahead of the sampled second phase signal Phase Sam2, the phase relationship may be determined to be 1. Conversely, in a case that the sampled first phase signal Phase Sam1 is behind the sampled second phase signal Phase Sam2, the phase relationship may be determined to be 0. As illustrated in FIG. 7, the phase relationship between the sampled first phase signal Phase Sam1 and the sampled second phase signal Phase Sam2 may be converted to a digital signal, which is indicated as binary numbers of 1 and 0.

However, the phase relationship between the sampled first phase signal Phase Sam1 and the sampled second phase signal Phase Sam2 may not be converted only to a binary digital signal, and thus the phase relationship may be converted to a base-N number in which N denotes a natural number greater than or equal to 2, for example, a ternary number, a quaternary number, and the like.

For example, in a case of converting the phase relationship between the sampled first phase signal Phase Sam1 and the sampled second phase signal Phase Sam2 to ternary numbers, the phase relationship may be converted to 0 when a phase difference between the sampled first phase signal Phase Sam1 and the sampled second phase signal Phase Sam2 is less than a first reference value, the phase relationship may be converted to 1 when the phase difference is greater than or equal to the first reference value and less than a second reference value that is greater than the first reference value, and the phase relationship may be converted to 2 when the phase difference is greater than or equal to the second reference value.

For another example, in a case of converting the phase relationship between the sampled first phase signal Phase Sam1 and the sampled second phase signal Phase Sam2 to quaternary numbers, the phase relationship may be converted to 0 when the phase difference between the sampled first phase signal Phase Sam1 and the sampled second phase signal Phase Sam2 is less than the first reference value, the phase relationship may be converted to 1 when the phase difference is greater than or equal to the first reference value and less than the second reference value that is greater than the first reference value, the phase relationship may be converted to 2 when the phase difference is greater than or equal to the second reference value and less than a third reference value that is greater than the second reference value, and the phase relationship may be converted to 3 when the phase difference is greater than or equal to the third reference value. Thus, in a case of converting the phase difference between the sampled first phase signal Phase Sam1 and the sampled second phase signal Phase Sam 2 to a base-N number, the phase difference between the sampled first phase signal Phase Sam1 and the sampled second phase signal Phase Sam2 to a base-N number, a magnitude of the phase difference between the sampled first phase signal Phase Sam1 and the sampled second phase signal Phase Sam2 may be compared to different N reference values, and a result of the comparing may be converted to the base-N number.

Here, in a case that a value of N is greater than 2, the binarizer 220 may be also referred to as a base-N number converter 220, and the base-N number converter 220 may compare the phase difference between the sampled first phase signal Phase Sam1 and the sampled second phase signal Phase Sam2 to different N reference values, and convert a result of the comparing to a base-N number.

The patterner 230 may divide the digital signal by a preset bit number into patterns. The patterner 230 may indicate, as histograms, the number of the patterns obtained by dividing the digital signal by the bit number. For example, the digital signal in which the phase difference is binarized may be divided by 3 bits each into eight patterns, for example, 000, 001, 010, 011, 100, 101, 110, and 111, and the number corresponding to each of the patterns may be indicated as the histograms. The bit number is not limited to 3 bits, and may vary depending on an observation time of the first brainwave signal EEG1 and the second brainwave signal EEG2 and the sampling period. To determine a complexity of a connection between brainwave signals, 2 bits or more may be desirably used.

The entropy analyzer 240 may calculate a PLE associated with a probability of each pattern being generated as illustrated in FIGS. 8 and 9 based on the histograms of the number corresponding to each pattern.

For example, in a case that a relationship in terms of leading and lagging behind between the first phase signal Phase1 and the second phase signal Phase2 is indicated as various patterns as illustrated in FIG. 8, the PLE may have a high value. For another example, in a case that the relationship in terms of leading and lagging behind between the first phase signal Phase1 and the second phase signal Phase2 is indicated as a simple pattern as illustrated in FIG. 9, for example, as in a case that the first phase signal Phase1 continuously lags behind the second phase signal Phase2 as indicated at a probability of a 000 pattern being generated and also is continuously ahead of the second phase signal Phase2 as indicated at a probability of a 111 pattern being generated, the PLE may have a low value. That is, using a PLE value based on a presence of a dominant pattern, a complexity of a connection between brainwave signals may be determined.

In addition, when a complexity of a connection between the first brainwave signal EEG1 and the second brainwave signal EEG2 increases, probabilities of the patterns being generated may be equalized, and thus the PLE may increase. Conversely, when the complexity of the connection between the first brainwave signal EEG1 and the second brainwave signal EEG2 decreases, a probability of a certain pattern being generated may increase, and thus the PLE may decrease. Further, when a depth of anesthesia increases, the complexity of the connection between the first brainwave signal EEG1 and the second brainwave signal EEG2 may decrease, and thus the PLE may decrease. Thus, the complexity of the connection between the first brainwave signal EEG1 and the second brainwave signal EEG2 may be calculated through an entropy analysis based on a probability of each pattern being generated.

Since a type of a dominant pattern may be different depending on a location at which the sensor 100 is disposed or a patient despite low entropy, a complexity of a connection between brainwave signals may be measured through a distribution of patterns in lieu of regularity of the patterns, and thus accuracy in measuring a depth of anesthesia may be improved.

The depth of anesthesia may be measured by analyzing the complexity of the connection between the brainwave signals by applying, as entropy information, a temporal pattern and a spatial pattern from a complexity of each of brainwaves detected in different regions through the phase information extractor 210 and the binarizer 220.

According to an example embodiment, dissimilar to related technology for modeling a complex mathematical structure based on an interaction between brainwave signals, a complexity of a connection between brainwaves may be rapidly measured by applying phase information, which is a simple mathematical model based on a continuity and a relationship of connections of information flows of a brain, and applying an entropy analysis based on the phase information.

According to an example embodiment, using phase information between brainwave signals in lieu of amplitude, an influence of noise due to internal and external elements may be minimized. In addition, using the phase information in lieu of an amplitude level of the brainwave signals, binarization may be more effective.

According to an example embodiment, using phase information between brainwave signals, a probability of an error occurring by a volume conduction may be resolved, and an error by a reference electrode may be prevented without using a reference signal.

<Calculator According to Another Example Embodiment>

Figure 10:
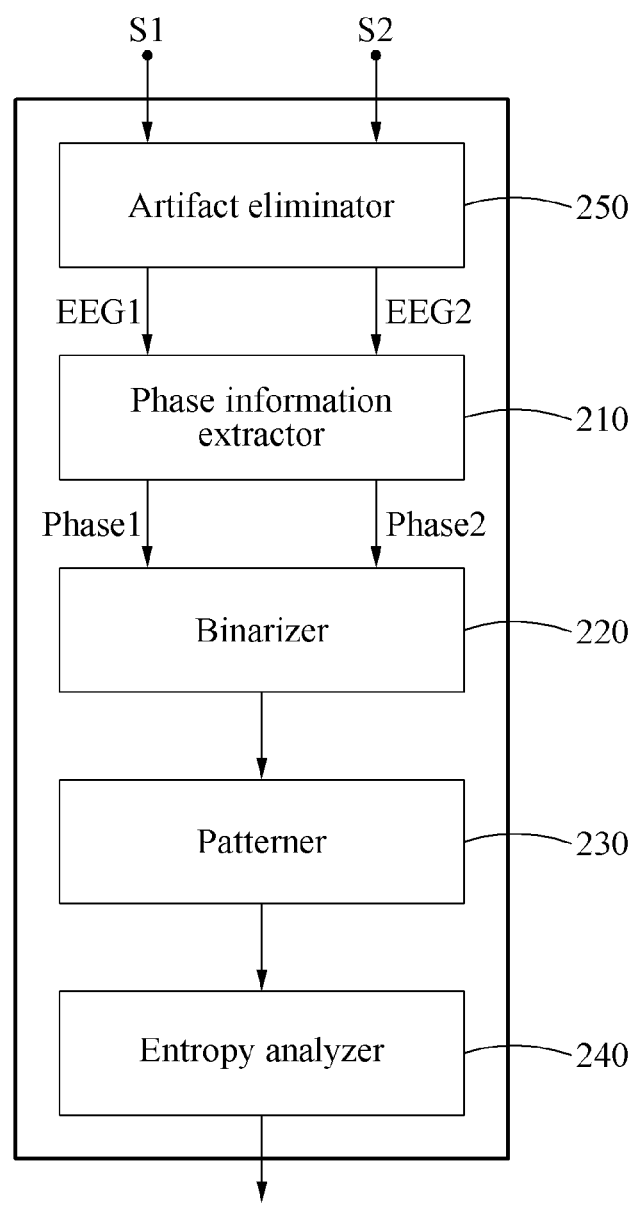
FIG. 10 is a diagram illustrating a calculator according to another example embodiment.

FIG. 10 is a diagram illustrating a calculator according to another example embodiment.

Referring to FIG. 10, the calculator 200 includes the phase information extractor 210, the binarizer 220, the patterner 230, and the entropy analyzer 240, and further includes an artifact eliminator 250.

The artifact eliminator 250, which is also referred to as a noise eliminator, may eliminate an artificial signal that is mixed in brainwave signals S1 and S2 sensed by the sensor 100.

A brainwave may be obtained by amplifying a microvoltage, and thus a micro-electric phenomenon may also be amplified and mixed in the brainwave. Thus, such an artificial signal may need to be eliminated. The artificial signal may include various types of noise, for example, artifacts derived from a human body itself including an electromyogram (EMG) of a head and neck portion, an electrooculogram (EOG) by an eye movement, and an electrocardiogram (ECG), and a movement artifact, for example, a potential change, by a head movement. In addition, other various types of noise may be originated by an external element, for example, ambient noise and vibration, a power supply issue, a mixture of a high frequency of peripheral electronic equipment, and a mixture of a high frequency of lighting equipment such as fluorescent and incandescent lights.

The artifact eliminator 250 may eliminate noise using, for example, an independent component analysis. A brainwave signal from which noise is eliminated may be input to the phase information extractor 210.

<Calculator According to Still Another Example Embodiment>

Figure 11:
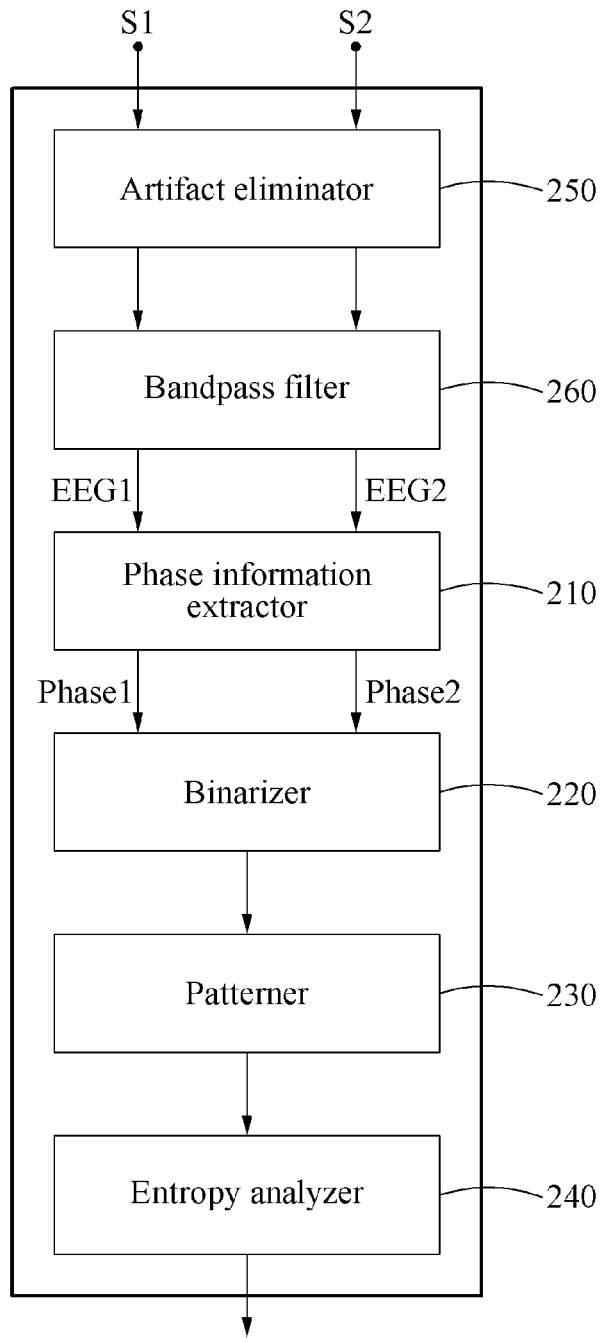
FIG. 11 is a diagram illustrating a calculator according to still another example embodiment.

FIG. 11 is a diagram illustrating a calculator according to still another example embodiment.

Referring to FIG. 11, the calculator 200 includes the phase information extractor 210, the binarizer 220, the patterner 230, the entropy analyzer 240, and the artifact eliminator 250, and further includes a bandpass filter 260.

A brainwave signal may include numerous noise components and only a limited signal component may be significant in signal classification, and thus the bandpass filter 260 may obtain only a signal component in a frequency band determined from a sensed brainwave signal through filtering and output the signal component obtained through the filtering to the phase information extractor 210.

<Calculator According to Yet Another Example Embodiment>

Figure 12:
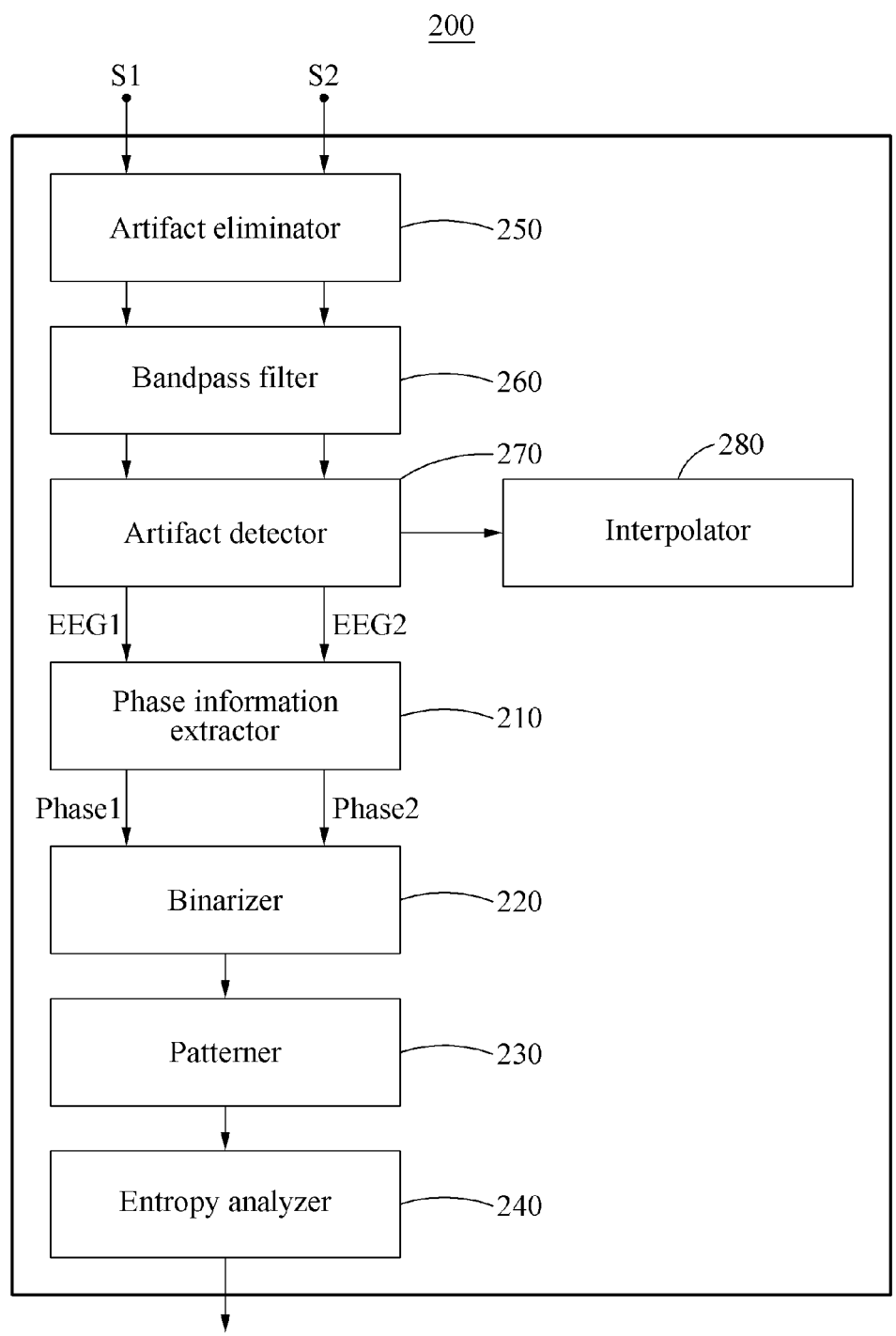
FIG. 12 is a diagram illustrating a calculator according to yet another example embodiment.

FIG. 12 is a diagram illustrating a calculator according to yet another example embodiment.

Referring to FIG. 12, the calculator 200 includes the phase information extractor 210, the binarizer 220, the patterner 230, the entropy analyzer 240, the artifact eliminator 250, the bandpass filter 260, and further includes an artifact detector 270.

The artifact detector 270 may verify whether noise is eliminated, by the artifact eliminator 250, from a brainwave signal sensed by the sensor 100 based on a signal output from the bandpass filter 260.

Since noise changes over time without having a permanently consistent characteristic, the artifact detector 270 may be an adaptive system based on a statistical characteristic of a noise signal.

The artifact detector 270 may include a linear estimator configured to separate a brainwave and noise from an input signal. Thus, the artifact detector 270 may determine a presence or absence of a noise component in or from a brainwave signal based on whether a separated noise component is present or absent, and a relative magnitude of the separated noise component.

In a case that noise is still included in the input brainwave signal, the artifact detector 270 may output the input brainwave signal to an interpolator 280 to be described hereinafter. In a case that the noise is eliminated, the artifact detector 270 may output the input brainwave signal to the phase information extractor 210.

The calculator 200 further includes the interpolator 280.

The interpolator 280 may calculate the input brainwave signal using interpolation to perform topographic mapping on three-dimensional or two-dimensional brain model, and output a result of the calculating to a storage.

<Method of Monitoring a State of Consciousness>

Figure 13:
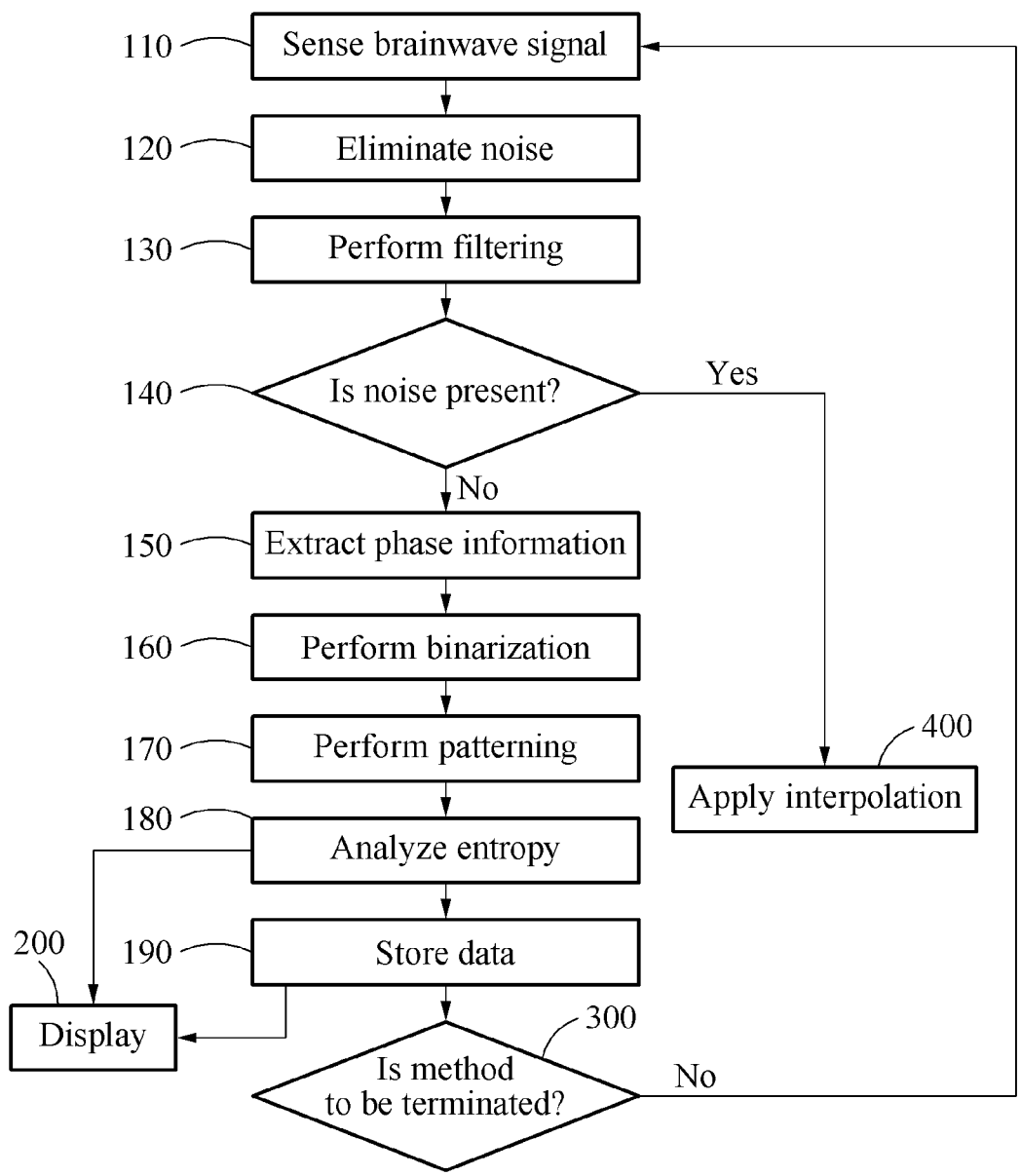
FIG. 13 is a flowchart illustrating a method of monitoring a state of consciousness according to an example embodiment.

FIG. 13 is a flowchart illustrating a method of monitoring a state of consciousness according to an example embodiment. Hereinafter, the method of monitoring a state of consciousness will be simply referred to as a consciousness state monitoring method.

Referring to FIG. 13, the consciousness state monitoring method includes operation 110 of sensing a brainwave signal, operation 150 of extracting phase information, operation 160 of performing binarization, operation 170 of performing patterning, operation 180 of analyzing entropy, and operation 200 of displaying.

In operation 110, a brainwave signal is detected from a human body using an electrode. The electrode may be the electrode portions 110 of the sensor 100 described above. The electrode may be classified into two electrodes, and the two electrodes may be a first electrode and a second electrode configured to sense a first brain wave and a second brainwave, respectively, from different portions of the human body during a preset time interval.

In operation 150, a first phase signal and a second phase signal are extracted, respectively, from the first brainwave signal and the second brainwave signal detected during the time interval.

In operations 160, 170, and 180, a PLE is calculated based on a variety of changes in a relationship between the first phase signal and the second phase signal in terms of leading and lagging behind. In detail, in operation 160, the binarization is performed on the relationship between the first phase signal and the second phase signal in terms of leading and lagging behind between the two signals by sampling each of the first phase signal and the second phase signal on a same sampling period and comparing respective sampling values corresponding to a same time.

Here, the binarization is not limited to binarizing a phase relationship between the sampled first phase signal, for example, Phase Sam1 as illustrated above, and the sampled second phase signal, for example, Phase Sam2 as illustrated above, to be a digital signal, and thus binarizing the phase relationship to be a base-N number in which N denotes a natural number greater than 2, for example, a ternary number, a quaternary number, and the like, may also be included in the binarization.

In a case that a value of N is greater than 2 in the base-N number, operation 160 of performing the binarization may be an operation of performing a base-N numeral system. Thus, in operation 160 of performing the base-N numeral system, the phase difference between the sampled first phase signal Phase Sam1 and the sampled second phase signal Phase Sam2 is compared to different N reference values, and a result of the comparing is converted to a base-N number.

In operation 170, a signal obtained through the conversion to the base-N number is divided into patterns having a preset bit number, and the number for each pattern is indicated as histograms. Here, a preset bit may be 2 or greater bits.

In operation 180, the PLE is calculated based on whether probabilities of each pattern being generated are equally distributed, or whether a probability is concentrated on a certain pattern. In detail, in a case that the probabilities of the patterns being generated are equally distributed, the PLE may have a high value. Conversely, in a case that a probability is concentrated on a certain pattern, the PLE may have a low value.

In operation 200, the PLE is represented by a numerical value, and the numerical value is displayed. For example, the PLE may be represented as a numerical value in a range from 0 to 100, and the PLE may be represented as one value among values 0 to 100.

The consciousness state monitoring method further includes operation 120 of eliminating noise, operation 130 of performing filtering, operation 140 of determining a presence or absence of noise, operation 400 of performing interpolation, operation 190 of storing data, and operation 300 of determining whether the consciousness state monitoring method is to be terminated.

In operation 120, noise mixed in the first sensed brainwave signal and the second sensed brainwave signal is eliminated therefrom. In operation 130, the first brainwave signal and the second brainwave signal from which the noise is eliminated is filtered to obtain a required frequency component in a certain frequency band. In operation 140, whether noise is present in the first brainwave signal and the second brainwave signal obtained through the filtering is determined in order to determine a presence of noise that is inappropriate as data for measuring a depth of anesthesia.

When the noise is not present in the first brainwave signal and the second brainwave signal obtained through the filtering, operation 150 is performed. Conversely, when the noise is present, operation 400 is performed. In operation 400, the interpolation is applied to the first brainwave signal and the second brainwave signal for using data for topographic mapping of a brain model. In operation 190, the first brainwave signal and the second brainwave signal to which the interpolation is applied are stored.

In addition, in operation 190, a result of analyzing the entropy is additionally stored. In operation 300, in a case that a complexity of a connection with another frequency component of the measured first brainwave signal and the measured second brainwave signal needs to be additionally detected, and/or in a case that a complexity of a connection between brainwave signals in different regions needs to be additionally detected, the operations described in the foregoing are performed repetitively.

According to an example embodiment, by analyzing a PLE based on a variety of changes in phase information between at least two brainwave signals, a complexity of a connection between the brainwave signals, the complexity reflecting a temporal change and a spatial change in the brainwave signals, may be calculated.

Using the phase information, an influence of internal and external noise may be minimized, and thus accuracy in measuring a depth of anesthesia may be improved. Thus, a complexity in calculating a PLE based on a single index such as, for example, a phase relationship, may be reduced significantly.

<Accuracy and Reliability Test in Measuring a Depth of Anesthesia Based on a PLE>

Figure 14:
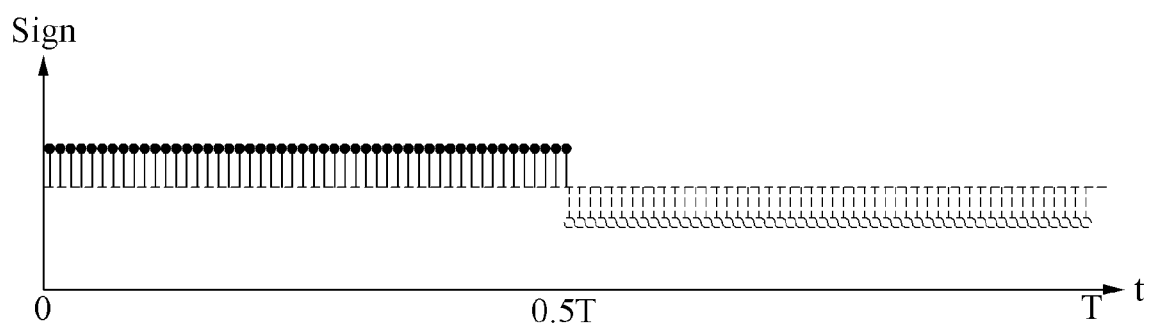
FIGS. 14 through 16 are binary graphs illustrating a relationship between two brainwave signals of which phases lead and lag behind based on time.
Figure 15:
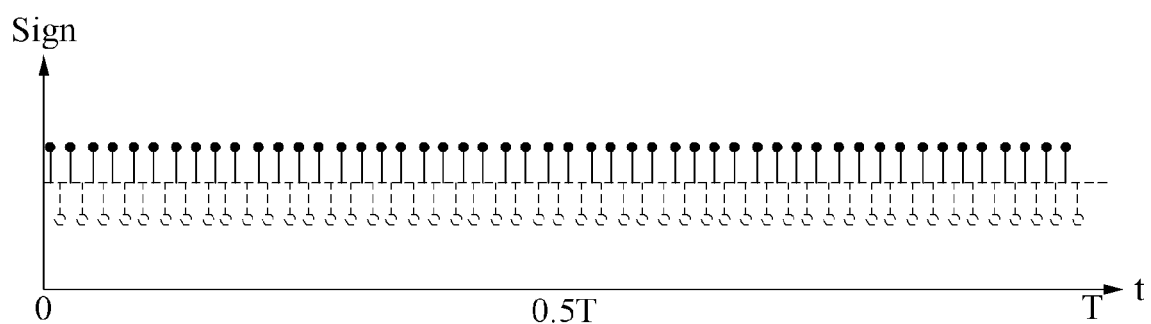
Figure 16:
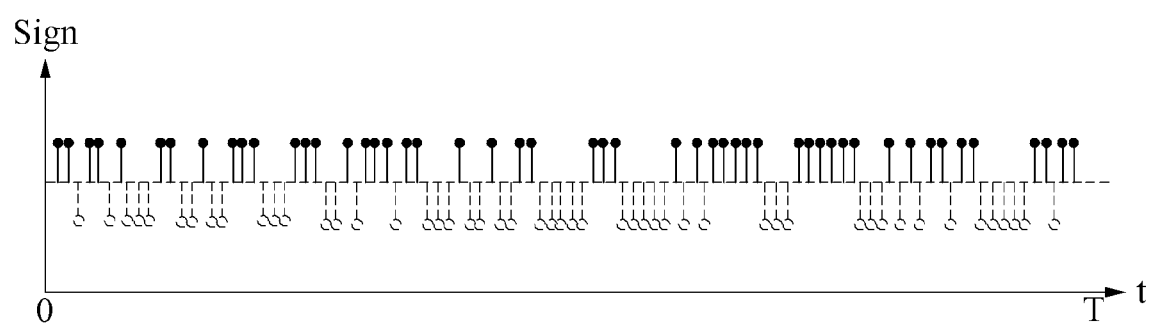

FIGS. 14 through 16 are binary graphs illustrating a relationship of two brainwave signals of which phases lead and lag behind based on time.

Referring to FIGS. 14 through 16, a half of data has a value of 1, and a remaining half of the data has a value of 0. Thus, a phase lag index (PLI) indicating a measurement of an imbalance of a distribution of a phase difference between two brainwave signals may have a value of 0. However, when analyzing a histogram for each of eight patterns obtained by dividing data by 3 bits as illustrated in FIG. 14, a PLE may have a first result value based on a single pattern, for example, a 110 pattern, and two dominant patterns, for example, a 111 pattern and a 000 pattern. When analyzing a histogram for each of the eight patterns obtained by dividing data by 3 bits as illustrated in FIG. 15, a PLE may have a second result value less than the first result value because only a 101 pattern is generated or shown. Also, when analyzing a histogram for each of the eight patterns obtained by dividing data by 3 bits as illustrated in FIG. 16, a PLE may have a third result value that is greater than the first result value and the second result value because all the eight patterns are generated or shown.

Using only the PLI indicating the measurement of the imbalance of the distribution of the phase difference, the data as illustrated in the graphs of FIGS. 14 through 16 may not be classified. However, based on the PLE, all the data as illustrated in the graphs of FIGS. 14 through 16 may be classified. Thus, according to an example embodiment, by assessing a complexity of a connection between two brainwave signals based on the PLE and measuring a depth of anesthesia, reliability of the measured depth of anesthesia may be greatly improved.

Figure 17:
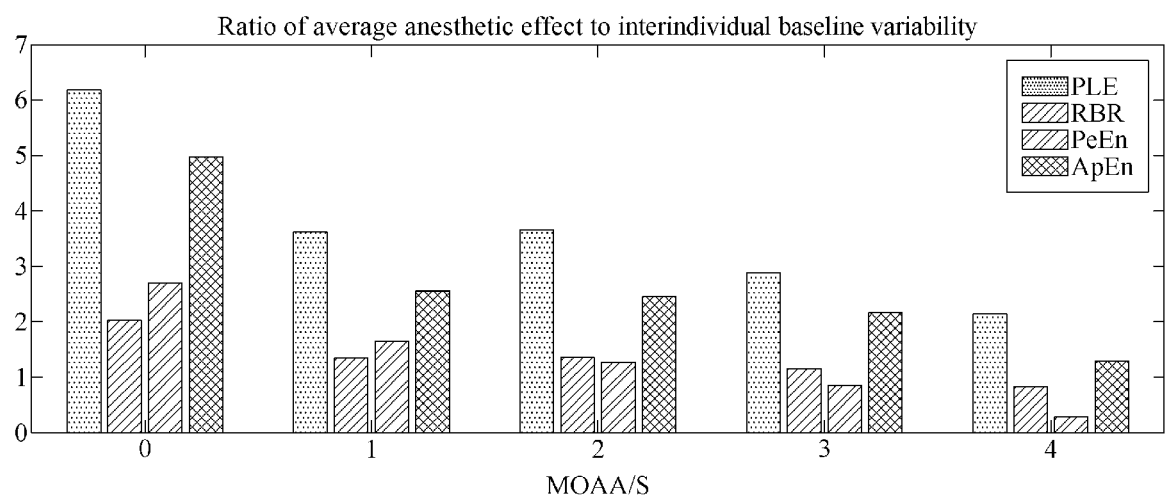
FIGS. 17 and 18 are diagrams illustrating a result of a modified observer's assessment of alertness and sedation (MOAA/S) indicated as a sedation assessment scale.
Figure 18:
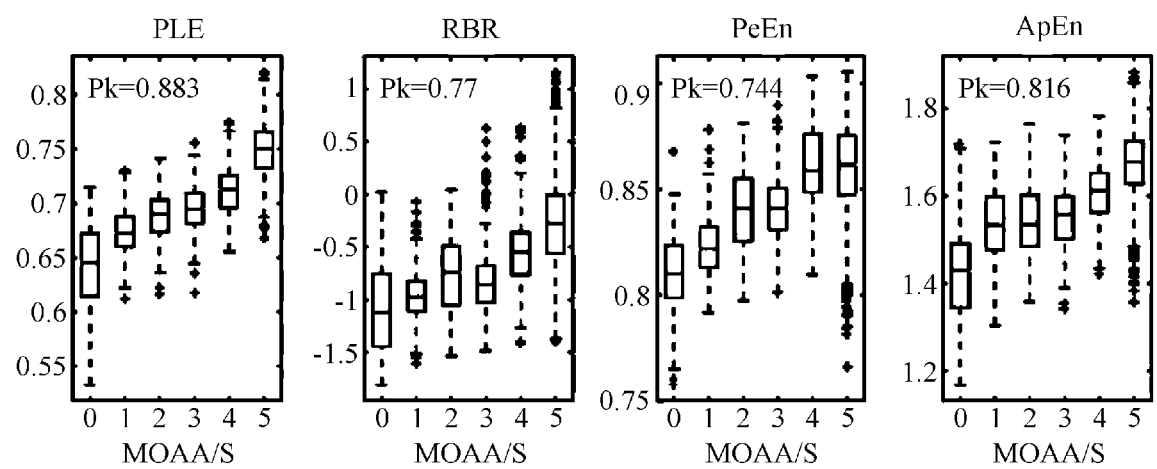

FIGS. 17 and 18 are diagrams illustrating a result of a modified observer's assessment of alertness and sedation (MOAA/S) indicated as a sedation assessment scale. A depth of sedation of a patient may be assessed based on each of a PLE, a relative beta ratio (RBR), a permutation entropy (PeEn), and an approximate entropy (ApEn) using an MOAA/S assessment method.

The RBR is an index assessing a depth of anesthesia based on a power ratio between gamma and alpha/beta. The ApEn is an index measuring a depth of anesthesia by assessing a complexity of a brainwave based on a low-dimensional dynamical system. The PeEn is an index assessing a depth of anesthesia based on a complexity of another brainwave.

The MOAA/S assessment method may classify a depth of sedation based on responsiveness to a voice command or a physical stimulus, and Table 1 below indicates a score of each type of response.

TABLE 1

| Responsiveness | Score |
| --- | --- |
| Responds readily to name spoken in 5 normal tone (alert) | 5 |
| Lethargic response to name spoken in normal tone | 4 |
| Responds only after name is called loudly 3 and/or repeatedly | 3 |
| Responds only after mild prodding or shaking | 2 |
| Does not respond to mild prodding or shaking | 1 |
| Does not respond to deep stimulus | 0 |

Referring to FIG. 17, compared to other assessment indices, a PLE has highest scores in a sedation assessment scale, for example, scores 3 and 4 indicating moderate sedation and scores 1 and 2 indicating deep sedation.

In addition, a prediction probability (Pk) is a value obtained by calculating a correlation with a depth of anesthesia based on a Narcotrend™ stages and the MOAA/S assessment method. Referring to FIG. 18, a PLE has a Pk of 0.883 (Pk=0.883), which is highest compared to other assessment indices. Thus, a PLE-based assessment of a depth of anesthesia according to an example embodiment may obtain highest reliability and accuracy, to compared to other assessment indices.

Figure 19:
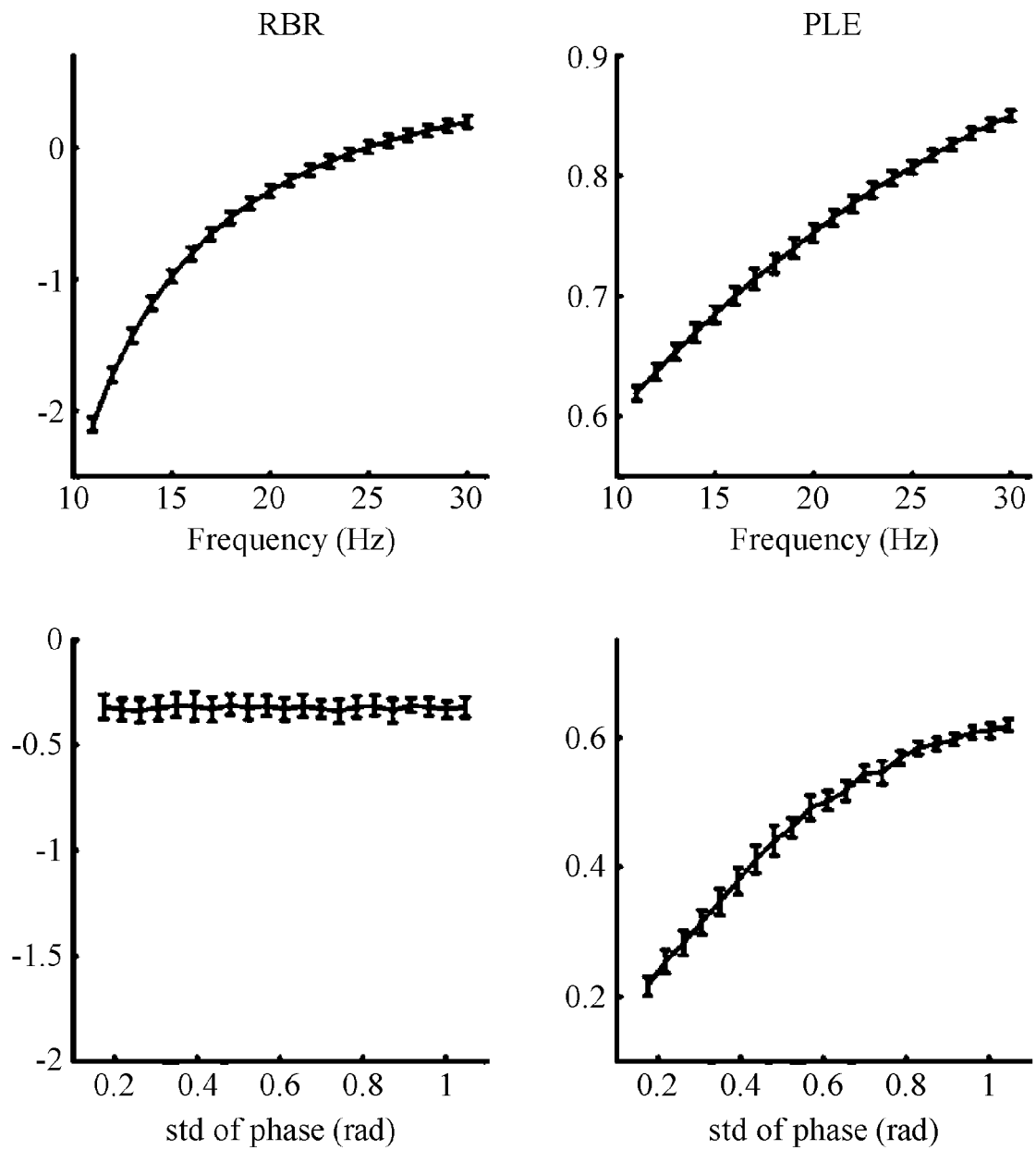
FIG. 19 is a graph illustrating the response of a relative beta ratio (RBR) and a phase lag entropy (PLE), with respect to changes in frequency and coherence.

FIG. 19 is a graph illustrating a frequency and coherence based on various mean frequencies and phase standard deviations.

FIG. 19 is a graph obtained through a simulation of a brainwave signal using an N-tori model (a paper entitled "Assessing functional connectivity from brain signals during general anesthesia," 13-15p, published in 2014 by Heonsoo Lee, and a paper entitled "Dynamical correlations on reconstructed invariant densities and their effect on correlation dimension estimation" published in International Journal of Bifurcation and Chaos volume 13, 723-732p (2003), by Galka A and Pfister G). By comparing an upper left graph and an upper right graph in FIG. 19, a PLE may be more sensitive to a change in mean frequency compared to an RBR. Also, referring to a lower right graph in FIG. 19, a PLE may decrease when a phase standard deviation decreases, for example, when coherence in a time series increases, and the number of digital signals corresponding to a 111 pattern and a 000 pattern increases. However, referring to a lower left graph in FIG. 19, an RBR does not track a change in coherence in a time series, dissimilar to the PLE as indicated.

Figure 20:
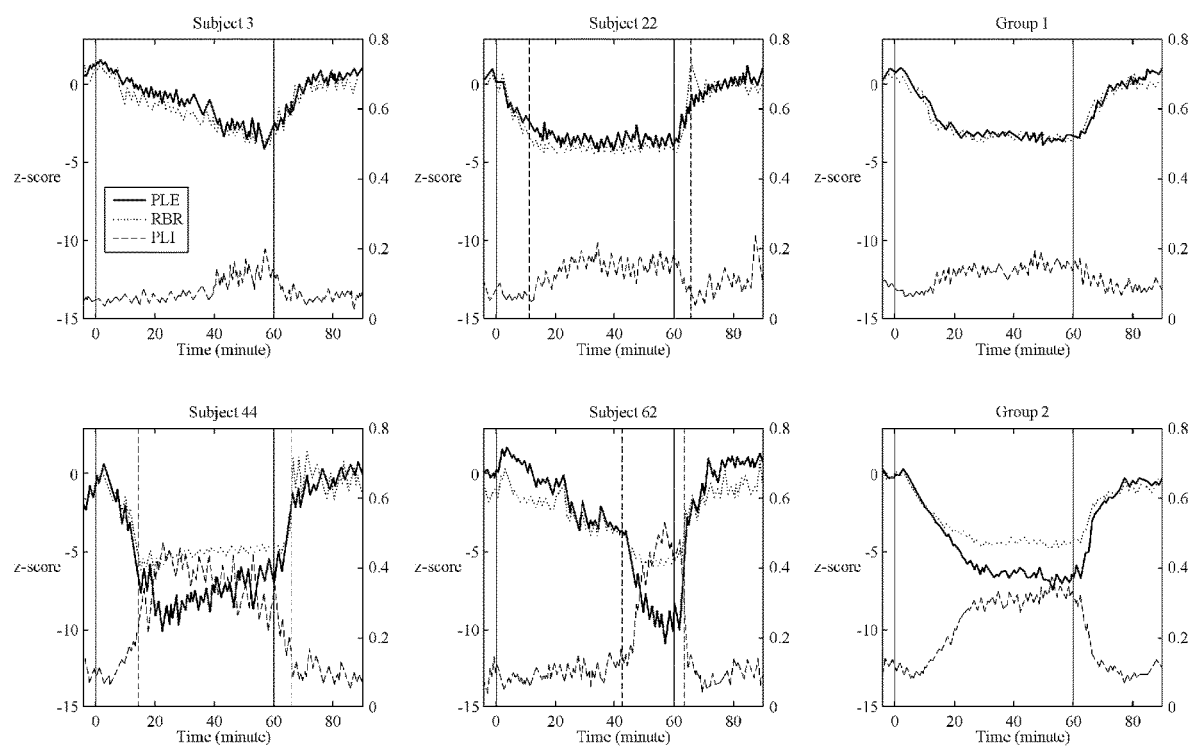
FIG. 20 is a graph illustrating a phase lag entropy (PLE), an RBR, and a phase lag index (PLI) based on a Z score.

FIG. 20 is a graph illustrating a PLE, an RBR, and a PLI based on a Z score.

A Z score is a standard score associated with a distribution from a reference point. A plurality of graphs in FIG. 20 illustrates normalized data of a PLE, an RBR, and a PLI during an observation of 60 minutes after injecting propofol into a patient. A first solid vertical line indicates a start of induction of anesthesia, and a second solid vertical line indicates an end of the induction of anesthesia. In addition, a first broken vertical line indicates a point in time of a transition from a conscious state to an unconscious state, and a second broken vertical line indicates a point in time of a transition from the unconscious state to the conscious state. A Z score of each of an RBR and a PLE may be calculated based on baseline data in a time interval between −4 and 0 minutes (min.) associated with initialization of the induction of anesthesia.

Referring to FIG. 20, in upper left and middle graphs in FIG. 20, a PLE and an RBR may show a similar tendency in two patients, for example, Subject 3 and Subject 22, showing no significant increase in PLI. In an upper left graph, an average waveform of a PLE and an average waveform of an RBR may be similar in a group Group 1 of four patients showing no significant increase in PLI. In lower left and middle graphs in FIG. 20, a PLE and an RBR may show a distinct difference in two patients, for example, Subject 44 and Subject 62, showing a significant increase in PLI during the injection of propofol. That is, when a PLI increases, a PLE may increase further compared to an RBR. In a lower right graph in FIG. 20, by analyzing an average waveform of a PLE and an average waveform of an RBR in a group Group 2 of 12 patients showing a significant increase in PLI, a PLE may be lowered further compared to an RBR when a PLI increases. Thus, according to an example embodiment, the PLE may be more effective in detecting an increase in spatial coordination between brainwave signals by anesthesia, in comparison to the RBR.

According to an example embodiment, accuracy and reliability in measuring a depth of anesthesia may be improved by analyzing a PLE based on a variety of changes in phase information between at least two brainwave signals, and by associating, with the depth of anesthesia, a complexity of a connection between the brainwave signals, the complexity reflecting a temporal change concept based on a change in coherence in a time series of a brainwave signal and a spatial region change including spatial coordination information between the brainwave signals.

According to example embodiments described herein, a method and apparatus for monitoring a state of consciousness may detect a complexity of a connection between at least two brainwave signals, and thus measure an influence of a connection between different brain regions on consciousness and simplify an information processing process in detecting the complexity of the connection between the brainwave signals. In addition, the method and apparatus may suggest a simple mathematical model-based algorithm associated with an interaction in a brain to verify a complexity of a connection between pieces of information of the brain based on a continuity of the connection between flows of the information in the brain and a relationship between the flows, and thus may measure a depth of anesthesia more rapidly and accurately.

The consciousness state monitoring method according to the above-described example embodiments may be recorded in various non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts.

For example, the method may be recorded in a non-transitory computer readable medium including program instructions to implement operations of sensing at least two brainwave signals, extracting a phase signal from each of the brainwave signals, patterning a phase difference between the extracted phase signals, calculating entropy based on a variety of generated patterns, and assessing a state of consciousness based on the calculated entropy.

The non-transitory computer-readable medium described herein refers to a medium configured to semi-permanently store data and be readable by a device, in lieu of a medium storing data for a short period of time such as, for example, a register, a cache, and a memory. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of monitoring a state of consciousness performed by at least one of processor of an apparatus, the method comprising:
   sensing at least two brainwave signals;
   extracting respective phase signals from the sensed brainwave signals;
   patterning a phase difference between the extracted phase signals;
   calculating entropy based on a variety of patterns; and
   displaying a state of consciousness assessed based on the calculated entropy on a display,
   wherein the patterning of the phase difference comprises converting a magnitude of the phase difference between the phase signals to a base-N number based on a result of comparing the magnitude of the phase difference and N reference values, wherein N denotes a natural number greater than or equal to 2.

2. The method of claim 1, wherein the brainwave signals in different cerebral regions are sensed.

3. The method of claim 1, wherein N denotes 2.

4. The method of claim 1, wherein the patterning of the phase difference comprises:
   dividing the phase difference converted to the base-N number into patterns based on a preset bit number.

5. An apparatus for monitoring a state of consciousness, the apparatus comprising:
   a sensor configured to sense at least two brainwave signals;
   a calculator configured to pattern a phase difference between respective phase signals of the sensed brainwave signals, and calculate entropy based on a variety of patterns; and
   a display configured to display the calculated entropy,
   wherein the calculator comprises:
   a phase information extractor configured to extract a first phase signal and a second phase signal, respectively, from the brainwave signals; and a base-N number converter configured to convert, to a base-N number, a magnitude of a phase difference between a sampled first phase signal and a sampled second phase signal obtained by sampling the extracted first phase signal and the extracted second phase signal based on a preset sampling period, based on a result of comparing the magnitude of the phase difference and N reference values, wherein N denotes a natural number greater than or equal to 2.

6. The apparatus of claim 5, wherein the calculator comprises:
a phase information extractor configured to extract a first phase signal and a second phase signal, respectively, from the brainwave signals.

7. The apparatus of claim 5, wherein the calculator comprises:
a phase information extractor configured to extract a first phase signal and a second phase signal, respectively, from the brainwave signals;
a base-N number converter configured to convert, to a base-N number, a magnitude of a phase difference between a sampled first phase signal and a sampled second phase signal obtained by sampling the extracted first phase signal and the extracted second phase signal based on a preset sampling period, based on a result of comparing the magnitude of the phase difference and N reference values, wherein N denotes a natural number greater than or equal to 2; and
a patterner configured to perform patterning on a digital signal converted from the base-N number to generate a pattern having a preset bit number.

8. The apparatus of claim 5, wherein the calculator comprises:
a phase information extractor configured to extract a first phase signal and a second phase signal, respectively, from the brainwave signals;
a base-N number converter configured to convert, to a base-N number, a magnitude of a phase difference between a sampled first phase signal and a sampled second phase signal obtained by sampling the extracted first phase signal and the extracted second phase signal based on a preset sampling period, based on a result of comparing the magnitude of the phase difference and N reference values, wherein N denotes a natural number greater than or equal to 2;
a patterner configured to perform patterning on a digital signal converted from the base-N number to generate a pattern having a preset bit number; and
an entropy analyzer configured to calculate entropy based on a variety of generated patterns.

9. A non-transitory computer-readable storage medium storing a program to cause computing hardware to:
sense at least two brainwave signals;
extract respective phase signals from the sensed brainwave signals;
pattern a phase difference between the extracted phase signals by converting a magnitude of the phase difference between the phase signals to a base-N number based on a result of comparing the magnitude of the phase difference and N reference values, wherein N denotes a natural number greater than or equal to 2;
calculate entropy based on a variety of patterns; and
display a state of consciousness assessed based on the calculated entropy on a display.

* * * * *